US010466216B2

(12) United States Patent
Wilks

(10) Patent No.: US 10,466,216 B2
(45) Date of Patent: Nov. 5, 2019

(54) CANNABINOID CONCENTRATION ANALYZER AND METHOD

(71) Applicant: ORANGE PHOTONICS, INC., Elkins, NH (US)

(72) Inventor: Dylan Elmer Wilks, New London, NH (US)

(73) Assignee: ORANGE PHOTONICS, INC., Elkins, NH (US)

( * ) Notice: Subject to any disclaimer, the term of this patent is extended or adjusted under 35 U.S.C. 154(b) by 162 days.

(21) Appl. No.: 15/253,107

(22) Filed: Aug. 31, 2016

(65) Prior Publication Data

US 2017/0059536 A1    Mar. 2, 2017

Related U.S. Application Data

(60) Provisional application No. 62/212,722, filed on Sep. 1, 2015.

(51) Int. Cl.
*G01N 30/86* (2006.01)
*G01N 30/74* (2006.01)
(Continued)

(52) U.S. Cl.
CPC ......... *G01N 30/8689* (2013.01); *G01N 30/02* (2013.01); *G01N 30/74* (2013.01); *G01N 30/88* (2013.01)

(58) Field of Classification Search
CPC .............. G01N 30/02; G01N 30/8689; G01N 2030/8648
See application file for complete search history.

(56) References Cited

U.S. PATENT DOCUMENTS

| | | | |
|---|---|---|---|
| 6,992,298 B2 * | 1/2006 | Nayfeh | B82Y 30/00 250/372 |
| 8,017,015 B2 * | 9/2011 | Clarke | B01J 20/28083 210/198.2 |

(Continued)

FOREIGN PATENT DOCUMENTS

JP       2002139484 A  *  5/2002  ........ B01J 20/28014

OTHER PUBLICATIONS

"Method of Resolving and Measuring Overlapping Chromatographic Peaks by Use of an On-Line Computer with Limited Storage Capacity" by Scott et al., Clinical Chemistry, vol. 16, No. 8, 1970, pp. 637-642.*

(Continued)

*Primary Examiner* — Justin N Olamit
(74) *Attorney, Agent, or Firm* — Morgan, Lewis & Bockius LLP

(57) ABSTRACT

A cannabinoid analysis system includes a solvent input port configured to receive a flow of a solvent, a sample input port configured to receive a chemical mixture including a sample, a pump configured to move the solvent and chemical mixture, an extraction cartridge coupled to the pump and configured to separate a combination of the chemical mixture and the flow of the solvent into two or more partially-separated chemical components, a spectroscopy cell configured to generate a chromatogram including two or more overlapping absorption peaks corresponding to the two or more partially-separated chemical components, and a controller configured to determine a chemical concentration of each partially-separated chemical component of the two or more partially-separated chemical components.

11 Claims, 5 Drawing Sheets

(51) Int. Cl.
*G01N 30/02* (2006.01)
*G01N 30/88* (2006.01)

(56) References Cited

U.S. PATENT DOCUMENTS

| | | | |
|---|---|---|---|
| 8,428,889 B2* | 4/2013 | Wright | G01J 3/28 |
| | | | 702/32 |
| 2009/0145205 A1* | 6/2009 | Hochgraeber | G01N 30/20 |
| | | | 73/61.55 |

OTHER PUBLICATIONS

"Correction Method for Quantitative Area Determination of Overlapping Chromatographic Peaks Based on the Exponentially Modified Gaussian (EMG) Model" by Binsheng et al., Journal of High Resolution Chromatography & Chromatography Communications, vol. 10, Aug. 1987, pp. 449-454.*

* cited by examiner

CANNABINOID CONCENTRATION ANALYZER AND METHOD

RELATED APPLICATION

This application claims the benefit of priority under 35 U.S.C. § 119(e) to U.S. Provisional Application No. 62/212,722, entitled "CANNABINOID CONCENTRATION ANALYZER," which was filed on Sep. 1, 2015. The content of the aforesaid application is hereby incorporated by reference in its entirety for all purposes.

BACKGROUND OF THE DISCLOSURE

Analysis of chemical samples may be performed using chromatography, spectroscopy, or a combination of both. Chromatography, which includes various techniques well-known to those of ordinary skill in the art (e.g., column chromatography, thin-layer chromatography, etc.), generally involves the separation of a chemical mixture into its constituent components. Spectroscopy is a known method of determining one or more properties of a sample of matter by observing the interaction of electromagnetic radiation with the sample. Generalized analysis techniques, utilizing the principles of chromatography, spectroscopy, or both, currently exist to analyze a wide variety of chemical samples including cannabis samples.

However, conventional generalized analysis techniques for determining the concentration of cannabinoids, such as Tetrahydrocannabinol (THC) and Cannabidiol (CBD), in chemical samples (e.g., cannabis samples) involve several drawbacks. Because the process is not specifically tailored to the cannabinoids of interest, the process is needlessly wasteful, involves extraneous equipment, and often requires a trained expert in chemical analysis. Accordingly, there is a need for a system that can easily be operated by an unskilled person and that is specifically designed to analyze the concentration of one or more cannabinoids of interest in a given sample.

SUMMARY

One aspect of the present disclosure is directed to a cannabinoid analysis system comprising a solvent input port configured to receive a flow of a solvent, a sample input port configured to receive a chemical mixture including a sample, a pump configured to move the solvent and chemical mixture, an extraction cartridge coupled to the pump and configured to separate a combination of the chemical mixture and the flow of the solvent into two or more partially-separated chemical components, a spectroscopy cell configured to generate a chromatogram including two or more overlapping absorption peaks corresponding to the two or more partially-separated chemical components, and a controller configured to determine a chemical concentration of each partially-separated chemical component of the two or more partially-separated chemical components.

In some embodiments, the spectroscopy cell further comprises one or both of a UV light source and an IR light source. The UV light source and the IR light source are configured to provide electromagnetic radiation to the two or more partially-separated chemical components. In at least one embodiment, the UV light source is configured to emit electromagnetic radiation having a wavelength of 230 nm. In some embodiments, the UV light source is configured to emit electromagnetic radiation having a wavelength of 230 nm, and the IR light source is configured to emit electromagnetic radiation having a wavelength of 3000 nm. In an embodiment, the UV light source is configured to emit electromagnetic radiation having a wavelength of 230 nm, and the IR light source is configured to emit electromagnetic radiation having a wavelength of 3000 nm, electromagnetic radiation having a wavelength of 5000 nm, electromagnetic radiation having a wavelength of 5700 nm, electromagnetic radiation having a wavelength of 6250 nm, electromagnetic radiation having a wavelength of 6900 nm, and electromagnetic radiation having a wavelength of 8000 nm.

In at least one embodiment, the spectroscopy cell includes a silicon carbide detector configured to receive the electromagnetic radiation. In some embodiments, the sample input port is configured to receive a calibration sample having a volume greater than a volume of the sample. In an embodiment, the two or more chemical components include two or more of cannabidiol, cannabidiolic acid, Δ9-tetrahydrocannabinol, tetrahydrocannabolic acid, cannabinol, cannabigerolic acid and cannabichromene. In some embodiments, the extraction cartridge is configured to execute a column chromatography procedure. In at least one embodiment, the extraction cartridge is a solid phase extraction cartridge.

Another aspect of the present disclosure is directed to a method of analyzing a cannabis sample in a cannabinoid analyzer is provided. In one embodiment, the method comprises acts of receiving a flow of a solvent, receiving a chemical mixture including a sample, combining the flow of the solvent and the chemical mixture, separating the combination of the flow of the solvent and the chemical mixture into two or more partially-separated chemical components, generating a chromatogram including two or more overlapping absorption peaks corresponding to the two or more partially-separated chemical components, and determining a chemical concentration of each partially-separated chemical component of the two or more partially-separated chemical components.

In some embodiments, the method includes acts of providing, by one or both of a UV light source and an IR light source, electromagnetic radiation to the two or more partially-separated chemical components. In at least one embodiment, the method includes an act of emitting, by the UV light source, electromagnetic radiation having a wavelength of 230 nm. In some embodiments, the method includes acts of emitting, by the UV light source, electromagnetic radiation having a wavelength of 230 nm, and emitting, by the IR light source, electromagnetic radiation having a wavelength of 3000 nm. According to one embodiment, the method includes acts of emitting, by the UV light source, electromagnetic radiation having a wavelength of 230 nm, and emitting, by the IR light source, electromagnetic radiation having a wavelength of 3000 nm, electromagnetic radiation having a wavelength of 5000 nm, electromagnetic radiation having a wavelength of 5700 nm, electromagnetic radiation having a wavelength of 6250 nm, electromagnetic radiation having a wavelength of 6900 nm, and electromagnetic radiation having a wavelength of 8000 nm.

In one embodiment, the method includes acts of receiving, by a silicon carbide detector, the electromagnetic radiation. In some embodiments, the method further includes acts of calibrating the cannabinoid analyzer responsive to receipt of a calibration sample having a volume greater than a volume of the sample. In an embodiment, the two or more chemical components include two or more of cannabidiol, cannabidiolic acid, Δ9-tetrahydrocannabinol, tetrahydrocannabolic acid, cannabinol, cannabigerolic acid and cannabichromene. In some embodiments, the act of separating the combination of the flow of the solvent and the chemical mixture includes executing a column chromatography procedure. In one embodiment, the act of executing the column chromatography procedure is performed in a solid phase extraction cartridge.

Still other aspects, examples, and advantages of these exemplary aspects and examples are discussed in detail below. Examples disclosed herein may be combined with other examples in any manner consistent with at least one of the principles disclosed herein, and references to "an example," "some examples," "an alternate example," "various examples," "one example" or the like are not necessarily mutually exclusive and are intended to indicate that a particular feature, structure or characteristic described may be included in at least one example. The appearances of such terms herein are not necessarily all referring to the same example.

BRIEF DESCRIPTION OF THE DRAWINGS

Various aspects of at least one example are discussed below with reference to the accompanying figures, which are not intended to be drawn to scale. The figures are included to provide illustration and a further understanding of the various aspects and examples, and are incorporated in and constitute a part of this specification, but are not intended as a definition of the limits of the invention. In the figures, each identical or nearly-identical component that is illustrated in various figures is represented by a like numeral. For purposes of clarity, not every component may be labeled in every figure. In the figures.

DETAILED DESCRIPTION

Aspects of the present disclosure are directed to systems and methods for the analysis of one or more cannabinoids present in a chemical sample (e.g., a cannabis sample). These systems and methods provide a lower-cost and easier-to-implement solution for analyzing chemical samples compared to conventional approaches. These benefits may be achieved by providing chemical analysis solutions specifically tailored to detecting the presence and concentration of specific cannabinoids of interest.

It is to be appreciated that examples of the methods and apparatus discussed herein are not limited in application to the details of construction and the arrangement of components set forth in the following description or illustrated in the accompanying drawings. The methods and apparatus are capable of implementation in other examples and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Figure 1:
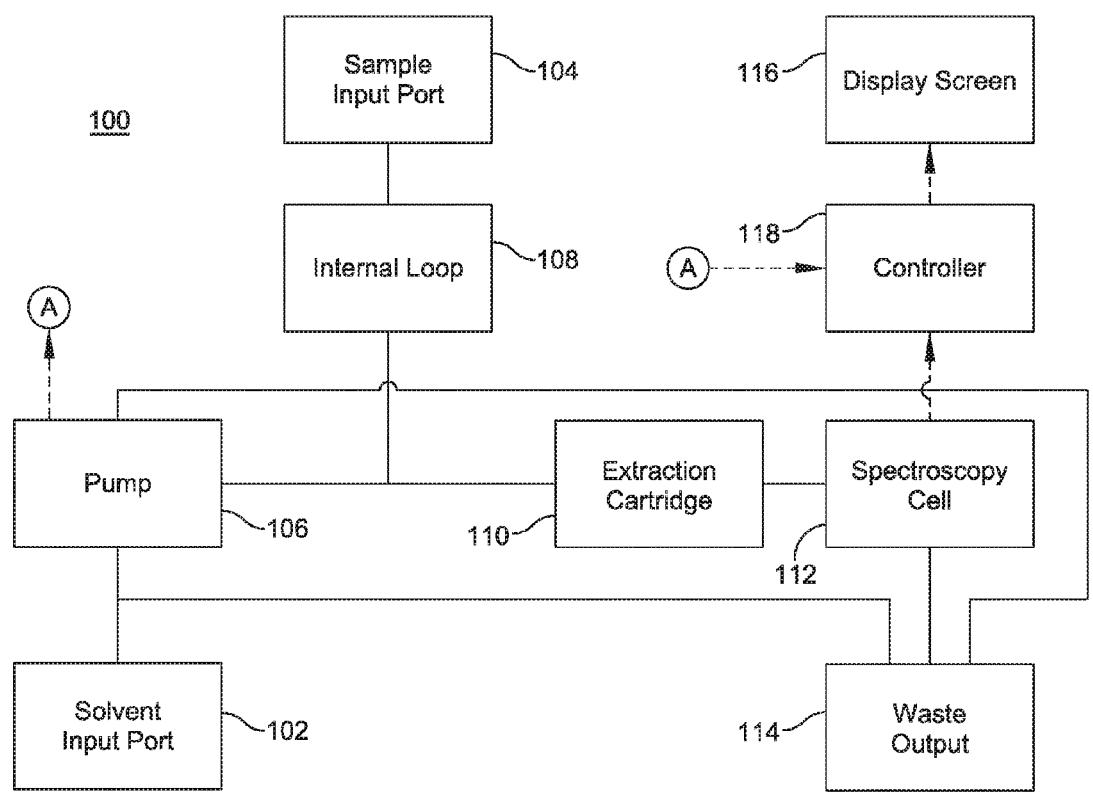
FIG. 1 is a schematic block diagram of a cannabinoid analyzer according to an embodiment of the present disclosure.

FIG. 1 illustrates a cannabinoid analyzer 100 according to one embodiment of the present disclosure. The cannabinoid analyzer 100 is specifically configured to analyze cannabinoids of interest including, for example, one or more of cannabidiol, cannabidiolic acid, Δ9-tetrahydrocannabinol, tetrahydrocannabolic acid, cannabinol, cannabigerolic acid and cannabichromene. In at least one embodiment, the cannabinoid analyzer 100 is configured to operate at pressures lower than those in conventional, more-generalized analyzers. This allows for a low-cost, replaceable, off-the-shelf separation column that enables higher flow speeds at lower pressures. The use of an off-the-shelf separation column leads to reduced separation of chemical component in a sample mixture but, as discussed in greater detail below with respect to FIG. 4, novel analysis techniques are employed to analyze chemical concentrations having reduced separation. In at least one embodiment, components that are necessary for operation in more-generalized analyzers, such as solvent degassers and column ovens, are unnecessary for proper operation of the cannabinoid analyzer 100 and may be omitted therefrom to reduce costs.

The cannabinoid analyzer 100 includes a solvent input port 102, a sample input port 104, a pump 106, an internal loop 108, an extraction cartridge 110, a spectroscopy cell 112, a waste output 114, a display screen 116 and a controller 118. The solvent input port 102 is configured to deliver a flow of a solvent to the pump 106 in a normal operating mode, and is configured to deliver solvent directly to the waste output 114 in an abnormal operating mode. The sample input port 104 is configured to deliver a mixture of a sample and a solvent to the internal loop 108 in a normal operating mode, and is configured to receive a mixture of sample particulates and the solvent in an abnormal operating mode. In a normal operating mode, the internal loop 108 is configured to receive the mixture of the solvent and the sample input port 104, and inject an amount of the sample and the solvent to the flow of the solvent driven by the pump 106 from the solvent input port 102. In an abnormal operating mode, the internal loop 108 is configured to provide a mixture of sample particulates and solvent to the sample input port 104.

The pump 106 is configured to drive fluid flow in the cannabinoid analyzer 100 such that, in a normal operating mode, solvent is drawn from the solvent input port 102, drawn through the pump 106 and provided to the extraction cartridge 110. The pump 106 further is configured to drive the mixture of the solvent and the sample received from the internal loop 108 to the extraction cartridge 110. In an abnormal operating mode, the pump 106 is configured to drive solvent from the solvent input port 102 directly to the waste output 114, and is configured to drive the mixture of the solvent and the sample particulates from the internal loop 108 out of the cannabinoid analyzer 100 via the sample input port 104. In at least one embodiment, operation of the pump 106 (e.g., in a normal operating mode, an abnormal operating mode, etc.) is controlled substantially by control signals (e.g., Pulse Width Modulation [PWM] signals) received from the controller 118.

The extraction cartridge 110 is configured to receive the mixture of the solvent and the sample from the internal loop 108 and the flow of solvent from the pump 106 in a normal operating mode, partially separate the mixture, and provide the partially-separated mixture to the spectroscopy cell 112. In an abnormal operating mode, the extraction cartridge 110 is configured to receive solvent and any available sample particulates from the spectroscopy cell 112, and provide the solvent and the sample particulates to the pump 106. In at least one embodiment, the extraction cartridge 110 is coupled to the internal loop 108 and to the spectroscopy cell 112 via a luer lock, a plurality of finger tight fittings, a combination of both, etc.

In a normal operating mode, the spectroscopy cell 112 is configured to receive a partially-separated mixture of the solvent and the sample from the extraction cartridge 110, perform a spectroscopy operation on the partially-separated mixture, and provide the partially-separated mixture to the waste output 114. Information collected from the spectroscopy operation is communicated to the controller 118 in the normal operating mode. In the abnormal operating mode, the spectroscopy cell 112 is configured to provide solvent and any sample particulates present in the spectroscopy cell 112 to the extraction cartridge 110. The controller 118 is configured to receive information from the spectroscopy cell 112, analyze the received information, and provide a graphical representation (e.g., a chromatogram, etc.) of the analyzed information to the display screen 116. The display screen 116 is configured to receive the graphical representation of the analyzed information from the controller 118 and display the graphical representation of the analyzed information for review by a user.

According to aspects of the disclosure, the pump 106 is configured to drive a direction of fluid flow in the cannabinoid analyzer 100. As will be described in greater detail below, the pump 106 drives the fluid flow in a first direction under normal operating conditions and drives the fluid flow in a second direction (e.g., opposite the first direction) under abnormal operating conditions (e.g., responsive to detection of a clog in one or more of the components of the cannabinoid analyzer 100 discussed above).

Figure 2:
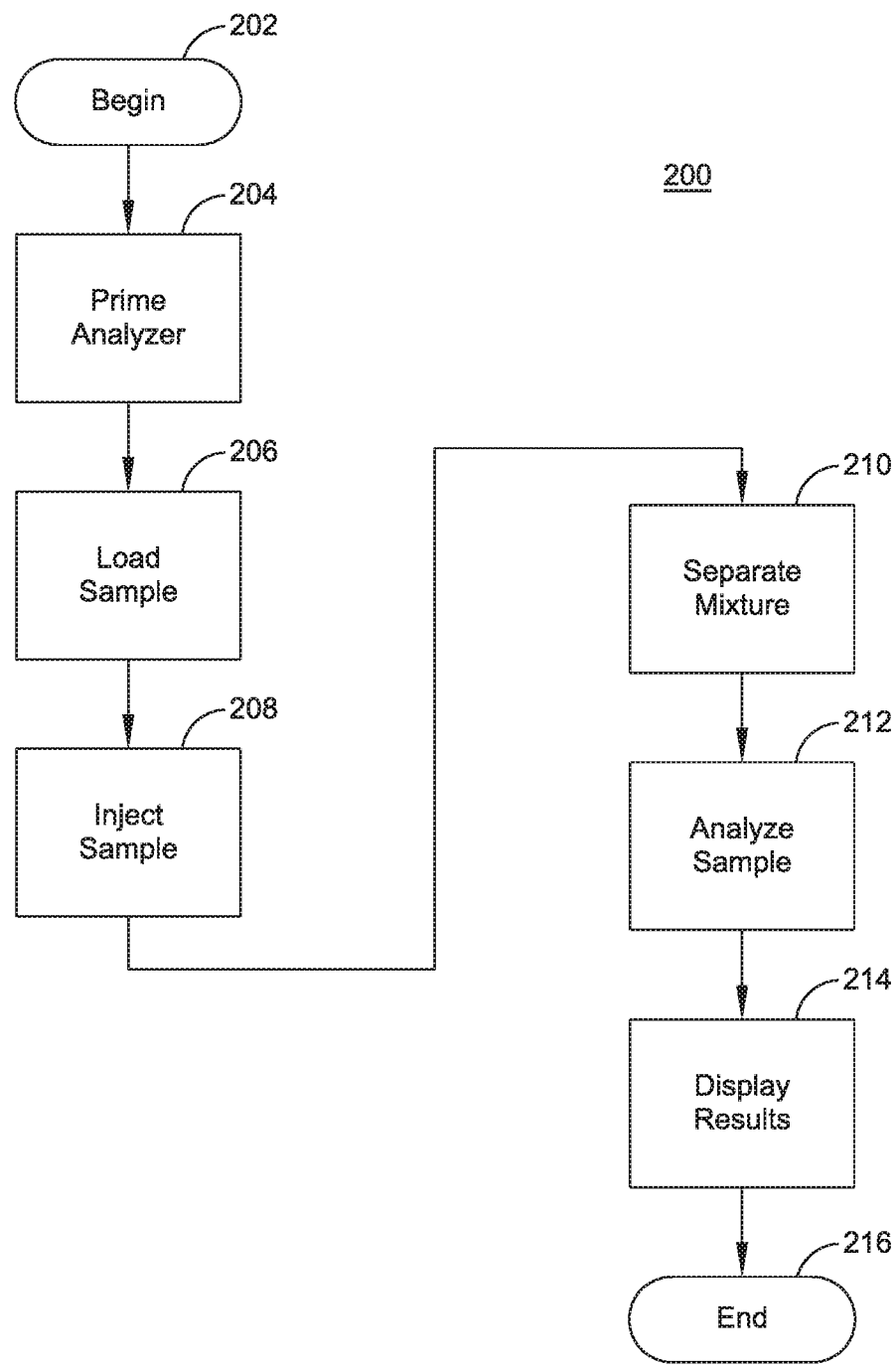
FIG. 2 is a process flow diagram of operation of the cannabinoid analyzer in a normal operating mode.

FIG. 2 illustrates a process 200 executed by the cannabinoid analyzer 100 to analyze a sample under normal operating conditions. At act 202, the process 200 begins. At act 204, the cannabinoid analyzer 100 is primed over a first window of time lasting, in one example, for approximately two minutes. The act 204 of priming the cannabinoid analyzer 100 includes actuating the pump 106 to draw a flow of a solvent from an external source into the solvent input port 102. The flow of the solvent is drawn from the solvent input port 102 and driven through the extraction cartridge 110 and the spectroscopy cell 112 to the waste output 114, thereby "wetting" the extraction cartridge 110 in preparation for sample analysis.

Providing the solvent to the spectroscopy cell 112 allows the spectroscopy cell 112 to perform a "zeroing" operation. As the solvent preferentially does not contain any cannabinoids of interest, the chemical composition of the solvent is captured during the zeroing operation to establish a baseline value. The baseline value subsequently can be compared to a chemical mixture containing one or more cannabinoids of interest such that any measured deviation from the baseline value can be attributed to the one or more cannabinoids of interest. In one embodiment, the solvent has a chemical composition of approximately 80% methanol and approximately 20% distilled, buffered water by volume. The buffer used in the water can include a combination of phosphoric acid and phosphoric acid salt (e.g., sodium phosphate monobasic dihydrate).

At act 206, the cannabinoid analyzer 100 receives a prepared sample (e.g., a cannabis sample combined with a solvent) via the sample input port 104, and loads the prepared sample into the internal loop 108. In one example, the internal loop 108 is an automated sample injector, such as a commercially-available RHEODYNE® injector provided by IDEX Health & Science LLC of Northbrook, Ill. Automated sample injectors such as the RHEODYNE valve include a loop that, when filled with a minimum volume of a sample, introduces the sample into a solvent flow with a reliable and consistent volume. The automated sample injector does not need to receive a specifically-desired volume of a sample; rather, provided that the loop is filled to the minimum volume, the injector will consistently introduce the specifically-desired amount of the sample into the flow of the solvent.

At act 208, the internal loop 108 provides the specifically-desired amount of the sample to the extraction cartridge 110. In one embodiment, the internal loop 108 transitions from a "loading phase" (e.g., a phase characterized by the internal loop 108 receiving the sample) to an "injection phase" (e.g., a phase subsequent to the "loading phase" characterized by the internal loop 108 providing the sample to the extraction cartridge 110) responsive to a valve (not pictured) being actuated from a first position to a second position. For example, the valve may be an external valve actuated by a user from the first position, corresponding to the loading phase, to the second position, corresponding to the injection phase, subsequent to the internal loop 108 being loaded with the minimum amount of the sample. In alternate embodiments, no user interaction is required, and the internal loop 108 is operable to automatically transition from the "loading phase" to the "injection phase" absent actuation of the valve.

At act 210, the extraction cartridge 110 receives the sample from the internal loop 108 and partially separates the received mixture into its constituent components. The extraction cartridge 110 executes a process of column chromatography to partially separate the received mixture using an appropriate amount (e.g., roughly 900 mg) of a packing material (e.g., octyl modified silica gel, octadecyl modified silica gel, etc.) and a solvent, and provides the partially-separated mixture to the spectroscopy cell 112. In at least one embodiment, the composition of the solvent used in the extraction cartridge 110 is substantially identical to that of the solvent that is received via the solvent input port 102 and via the sample input port 104.

At act 212, the spectroscopy cell 112 analyzes the partially-separated sample received from the extraction cartridge 110 to detect the concentration of selected cannabinoids of interest in the sample. Analysis of the presence of cannabinoids of interest in the partially-separated sample is discussed in greater detail below with respect to FIG. 3.

At act 214, the results of the analysis performed at act 212 are displayed on the display screen 116 of the cannabinoid analyzer 100. For example, the results can include concentrations (e.g., measured from 0-100% of cannabinoid content) of each cannabinoid of the one or more selected cannabinoids of interest discussed above. The results can be saved in a memory permanently or removably coupled to the cannabinoid analyzer 100 (e.g., on a hard drive, on a USB drive, etc.), and may be communicated via a wireless (e.g., via Wifi, Bluetooth, etc.) or wired connection to an external storage entity including, for example, a mobile phone, a cloud-based storage medium, etc. At act 216, the process 200 ends.

In at least one embodiment, a calibration procedure is executed prior to analysis of a sample (e.g., a cannabis sample). The calibration procedure is substantially identical to a process of analyzing a sample (e.g., the process 200 discussed above with respect to FIG. 2), except that the sample is replaced by a calibration sample. The chemical composition of the calibration sample by volume is substantially identical to the chemical composition of the sample by volume. However, the calibration sample is injected into the cannabinoid analyzer 100 with a much higher volume (e.g., at least 12 times larger) than that of the sample. In alternate embodiments, the calibration sample may have the same volume as the sample or a lower volume than the sample. In further embodiments, no calibration procedure is executed.

Figure 3:
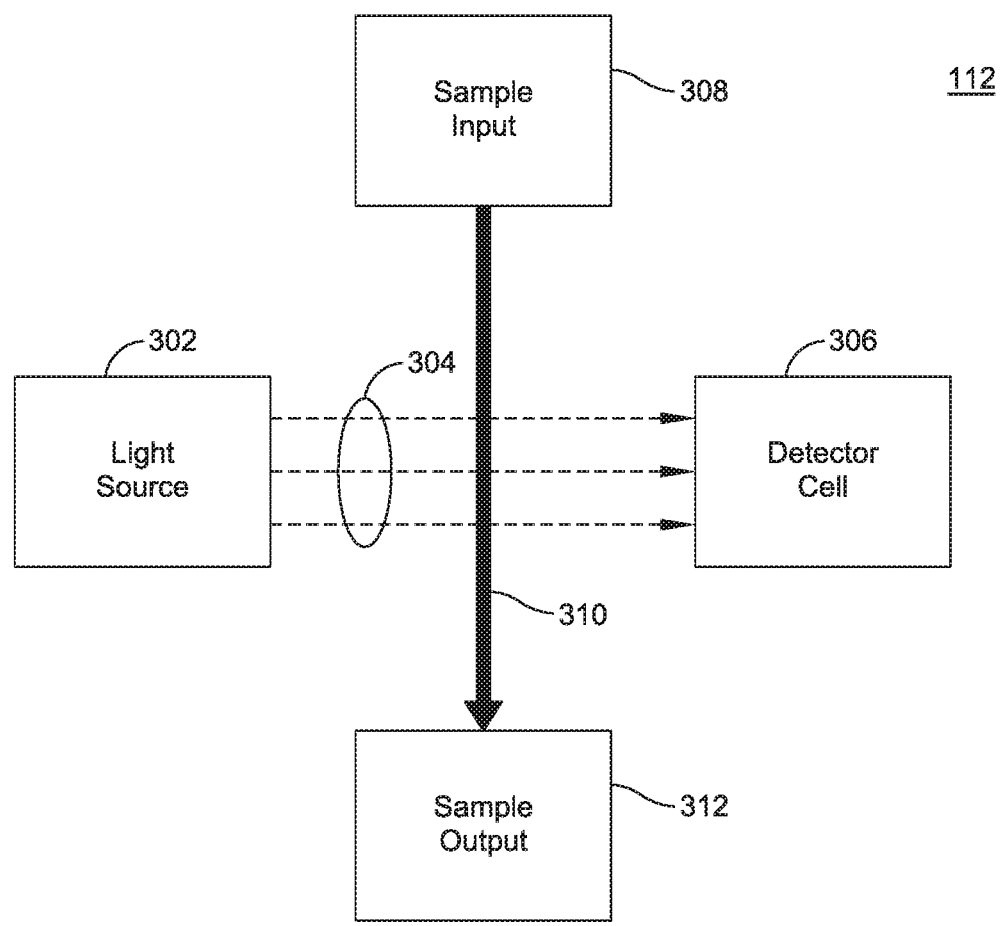
FIG. 3 is a schematic block diagram of a spectroscopy cell according to an embodiment.

FIG. 3 illustrates a more detailed view of the spectroscopy cell 112 according to one embodiment. The spectroscopy cell 112 includes a light source 302 configured to emit electromagnetic radiation 304, a detector cell 306 configured to receive the electromagnetic radiation 304, and a sample input 308 configured to provide a flow of a sample 310 to a sample output 312.

In aspects of the present disclosure, the electromagnetic radiation 304 includes one or more of UltraViolet (UV) light, InfraRed (IR) light, or other wavelengths of electromagnetic radiation. In a first embodiment, the electromagnetic radiation 304 can include UV light having a wavelength of approximately 230 nanometers (nm). In alternate embodiments, the electromagnetic radiation 304 may include UV electromagnetic radiation of approximately 230 nm in combination with one or more of: (i) 3000 nm electromagnetic radiation; (ii) 275 nm and 310 nm electromagnetic radiation; and (iii) 3000 nm, 5000 nm, 5700 nm, 6250 nm, 6900 nm and 8000 nm electromagnetic radiation.

Generally speaking, the light source 302 (e.g., a solid state Light Emitting Diode (LED), a Micro-Electro-Mechanical System (MEMS)-based IR light source, etc.) passes the electromagnetic radiation 304 (e.g., UV light, IR light, a combination of UV and infrared light, etc.) through the flow of the sample 310 to the detector cell 306 (e.g., a silicon carbide detector, a lithium tantalite detector coupled to one or more optical filters, etc.). The electromagnetic radiation 304 interacts with, and is partially absorbed by, one or more cannabinoids of interest present in the flow of the sample 310. The detector cell 306 analyzes the received electromagnetic radiation 304 to determine the wavelengths of the electromagnetic radiation 304 at which the partial absorption occurs and, using the partial absorption data, determines the concentrations of each of the one or more cannabinoids of interest present in the flow of the sample 310. In some embodiments, the detector cell 306 is operable to communicate the partial absorption data to the controller 118, and the controller 118 is operable to determine the concentrations of each of the one or more cannabinoids of interest present in the flow of the sample 310.

In conventional, generalized chemical analysis systems having expensive chromatography systems, chemical mixtures are finely and distinctly separated before spectroscopy is performed. In at least one embodiment of the present disclosure, the extraction cartridge 110 performs a coarser separation of the chemical mixture received from the internal loop 108. Accordingly, the spectroscopy cell 112 may receive a sample that has not been fully and distinctly separated into its constituent components and, subsequent to analysis of the received sample (e.g., by the controller 118), a chromatogram having two or more overlapping absorption peaks may be produced. The interference of one absorption peak with another must be corrected for in order to derive meaningful information from the chromatogram.

As will be described in greater detail below, the controller 118 can be configured to correct for the interference discussed above. Using data stored in associated memory, the controller 118 is operable to execute one or more instructions that may result in manipulated data. In some examples, the controller 118 can include one or more processors or other types of controllers. The controller 118 may perform a portion of the functions discussed herein on a processor, and perform another portion using an Application-Specific Integrated Circuit (ASIC) tailored to perform particular operations. As illustrated by the examples described herein, examples in accordance with the present invention may perform the operations described herein using many specific combinations of hardware and software and the invention is not limited to any particular combination of hardware and software components.

Figure 4:
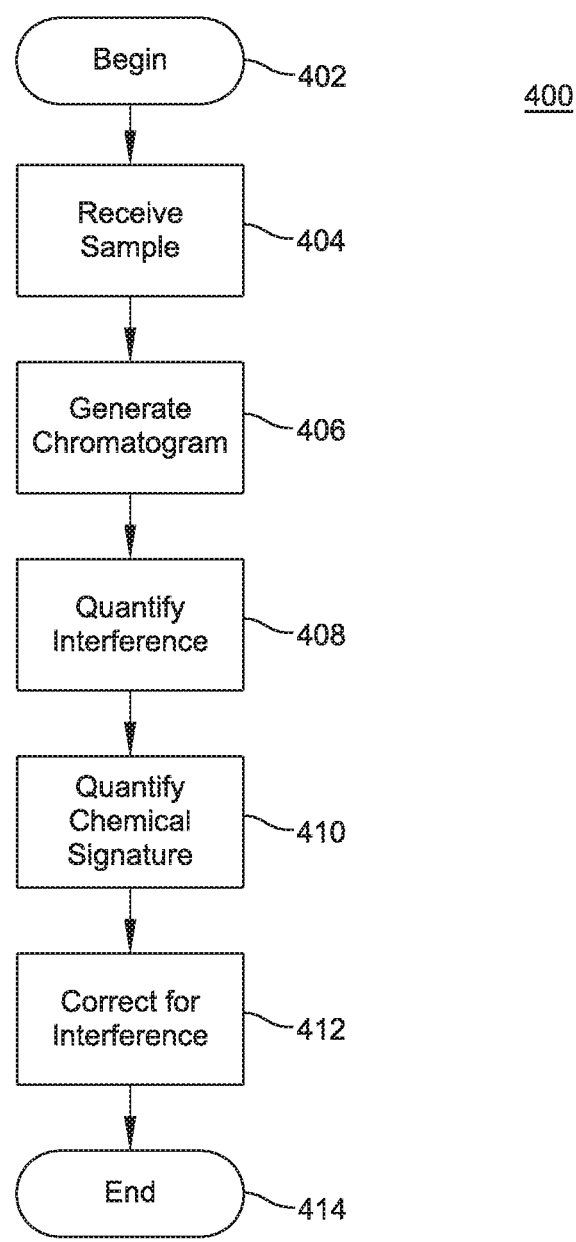
FIG. 4 is a process flow diagram of analyzing a partially-separated chemical mixture.

FIG. 4 illustrates a process 400 of determining individual chemical component concentrations from a partially-separated sample. At act 402, the process 400 begins. At act 404, the spectroscopy cell 112 receives a partially-separated sample. At act 406, spectroscopic data is collected from the sample to generate a chromatogram having one or more chemical signatures (e.g., absorption peaks). For example, the act 406 can include measuring, by the detector cell 306, electromagnetic radiation 304 received from the light source 302 (e.g., for approximately eight minutes at a rate of two measurements per second in one embodiment) and sending the measurements to the controller 118 for further analysis.

At act 408, the controller 118 quantifies a degree of interference between the chemical signatures in the chromatogram generated at act 406. For example, if the partially-separated sample includes a first chemical component and a second chemical component, the controller 118 quantifies a first interference factor descriptive of a degree to which a chemical signature of the first chemical component overlaps with, and thus interferes with, a chemical signature of the second chemical component. The controller 118 further quantifies a second interference factor descriptive of a degree to which the chemical signature of the second chemical component overlaps with, and thus interferes with, the chemical signature of the first chemical component.

At act 410, the controller 118 quantifies the chemical signature of the first chemical component and the chemical signature of the second chemical component. At act 412, the controller 118 corrects the quantification of the chemical signature of the first chemical component by using the second interference factor to eliminate the interference of the second chemical signature with the first chemical signature. The controller 118 further corrects the quantification of the chemical signature of the second chemical component by using the first interference factor to eliminate the interference of the first chemical signature with the second chemical signature. At act 414, the process 400 ends.

One solution to determining individual chemical component concentrations from a partially-separated sample is as follows. A square matrix is created having N rows and N columns, where N is the number of chemical components present in the partially-separated sample. Each column of the square matrix corresponds to a respective chemical component of the N chemical components, and each row of the square matrix corresponds to a chemical component that interferes with each respective chemical component. Each cell of the N×N matrix includes an interference factor between chemical components of the partially-separated sample. For example, if 20% of a chemical signature of a first chemical component is contributed by interference from a chemical signature of a second chemical component (e.g., due to the chemical signatures overlapping), then the interference factor will be 0.2, and will appear in the intersection of the first column and the second row. It is to be appreciated that, in each of the principal diagonal cells of the square matrix, an interference factor of 1 will be present to indicate that a chemical component overlaps itself entirely.

Responsive to completing the construction of the square matrix, the inverse of the square matrix is taken to create an inverted matrix. The inverted matrix is multiplied by an N×1 matrix to produce a corrected matrix, wherein each cell of the N×1 matrix includes a quantification of a chemical signature (e.g., an area of an absorption peak) for each of the N chemical signatures. The corrected matrix is an N×1 matrix, wherein each cell of the corrected matrix includes a quantification of each chemical signature of the N chemical signatures corrected for interference from each other chemical signature of the N chemical signatures. The contents of the corrected matrix are transformed into relative concentration data and displayed (e.g., via the display screen 116) for review by a user.

It is to be appreciated, in view of the foregoing, that an embodiment of the present disclosure provides a low-cost solution to chemical analysis of chemical samples, wherein cost reduction is accomplished at least in part through implementation of a low-cost extraction cartridge 110. In at least one embodiment, the extraction cartridge 110 does not separate a received chemical mixture into its constituent elements as finely as conventional approaches to chromatography. Embodiments described herein, such as those described in FIG. 4, provide a solution to analyzing partially-separated mixtures to quantify concentrations of each of the constituent elements accurately.

Furthermore, it is to be appreciated that the cannabinoid analyzer 100 is operable to analyze chemical samples derived from various forms. However, in at least one embodiment, the cannabinoid analyzer 100 is preferably configured to receive a sample that has been prepared for analysis prior to injection into the sample input port 104. Preparation of the sample according to aspects of the present disclosure generally includes combining (e.g., by shaking, either manually or by a machine) a prescribed quantity of a sample with a prescribed quantity of a solvent in a vial, extracting a portion of the combination of the solvent and the sample from the vial with a syringe, and injecting the extracted portion into the sample input port 102 of the cannabinoid analyzer 100 through a filter coupled to the syringe.

In at least one embodiment, the prescribed quantities are calculated by the cannabinoid analyzer 100 and displayed on the display screen 116. For example, for samples containing low concentrations of a cannabinoid (e.g., 0-33% concentration of the cannabinoid, any other selected range, etc.) selected by a user, the cannabinoid analyzer 100 may specify, on the display screen 116, a relatively large amount of the sample (e.g., roughly 100 mg) to be combined with a relatively small amount of the solvent (e.g., roughly 10 ml). For samples containing high concentrations of a cannabinoid (e.g., 30-100% concentration of the cannabinoid, any other selected range, etc.), the cannabinoid analyzer 100 may specify a relatively small amount of the sample (e.g., roughly 50 mg) to be combined with a relatively large amount of the solvent (e.g., roughly 15 ml). As discussed above, the solvent combined with the sample may be substantially identical to the solvent received by the cannabinoid analyzer 100 via solvent input port 102, advantageously simplifying the analysis procedure discussed above with respect to FIG. 2 by reducing the required number of components to be used with the cannabinoid analyzer 100.

The sample can be derived from one of several forms including, for example, dry samples, wet samples, extract samples, edible substances, etc. Samples in a substantially solid state (e.g., dry samples, edible substances, etc.) may require additional preparation before being combined with the solvent. For example, the sample may be a cannabis flower that needs to be ground (e.g., using any suitable commercially-available grinder) into a ground form prior to combination with the solvent. Samples in a substantially liquid state (e.g., wet samples, extract samples, etc.) may not require additional preparation, and can be combined directly with the solvent.

Improper preparation of certain samples, such as dry samples, may negatively impact components of the cannabinoid analyzer 100, such as by obstructing fluid flow in one or more of the components (e.g., in the internal loop 108, the extraction cartridge 110, the spectroscopy cell 112, etc.) due to an undesirable accumulation of sample particulates. Operating the cannabinoid analyzer 100 in a normal operating mode, as discussed above with respect to FIG. 2, despite an obstruction of fluid flow may negatively impact one or more of the components 102-114 of the analyzer and may negatively impact the efficacy of the analyzer as a whole. Accordingly, in some embodiments it may be desirable to remove the obstruction of fluid flow prior to resuming execution of the normal operating mode discussed above with respect to FIG. 2.

Figure 5:
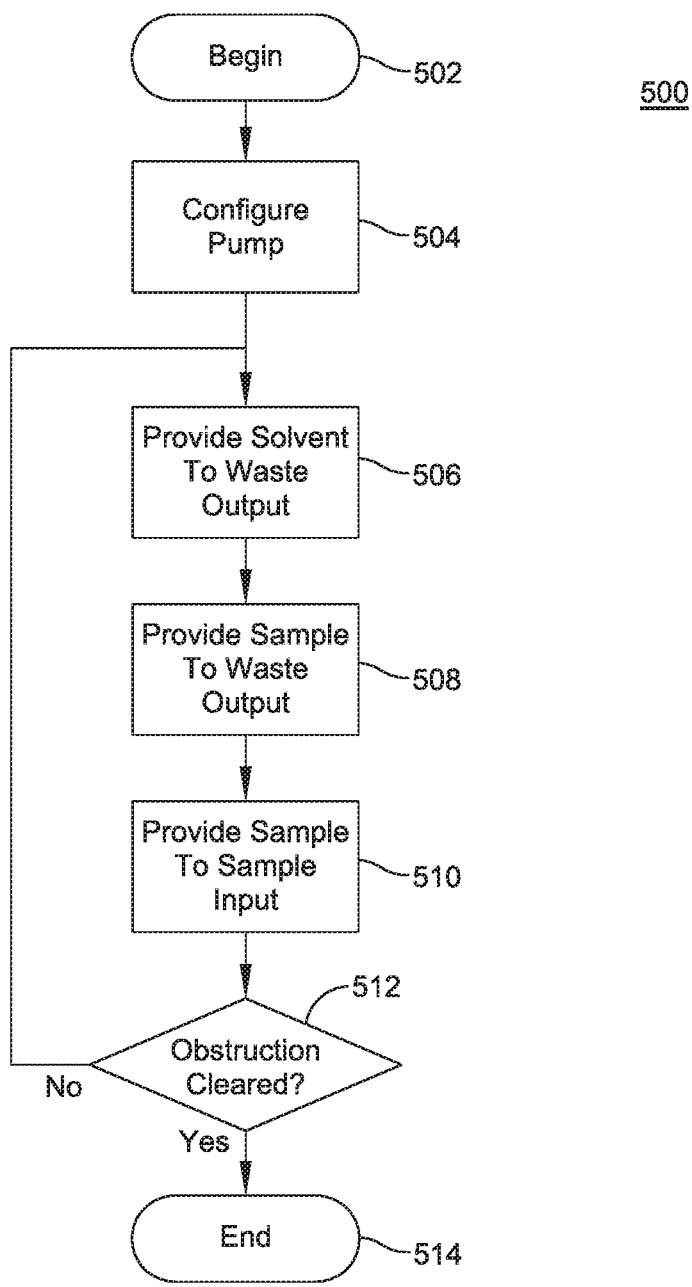
FIG. 5 is a process flow diagram of operation of the cannabinoid analyzer in an abnormal operating mode.

FIG. 5 illustrates a process 500 for operating the cannabinoid analyzer 100 in an abnormal operating mode. For example, the process 500 may be executed responsive to detection of an obstruction of fluid flow in the cannabinoid analyzer 100 caused, in the illustrated embodiment, by an accumulation of sample particulates in one or more of the internal loop 108, the extraction cartridge 110 and the spectroscopy cell 112.

At act 502, the process 500 begins. At act 504, the pump 106 is configured. For example, the act 504 can include configuring the pump 106 to drive fluid flow in the cannabinoid analyzer 100 in a direction opposite the direction of the fluid flow in the normal operating mode. At act 506, solvent received at the solvent input port 102 is driven by the pump 106 directly to the waste output 114. At act 508, a mixture of the solvent and the accumulation of sample particulates in one or more of the extraction cartridge 110 and the spectroscopy cell 112 is drawn through the pump 106 to the waste output 114. At act 510, the pump 106 drives solvent through the internal loop 108 and out of the cannabinoid analyzer 100 via the sample input port 104. At act 512, an evaluation is made as to whether the accumulation of sample particulates has been removed. If the accumulation of sample particulates has not been cleared (512 NO), then the process 500 returns to act 506. If the accumulation of sample particulates has been cleared (512 YES), then the process 500 terminates at act 514.

While particular aspects and implementations of the present disclosure have been illustrated and described, it is to be understood that the present disclosure is not limited to the precise construction and compositions disclosed herein and that various modifications, changes, and variations are not only contemplated but also apparent from the foregoing descriptions without departing from the scope of the present disclosure as defined in the appended claims.

For example, although FIG. 3 illustrates the electromagnetic radiation 304 as traveling substantially perpendicularly to the flow of the sample 310, in alternate embodiments, the electromagnetic radiation 304 may travel in a substantially parallel path with the flow of the sample 310. Such an embodiment may be implemented using a substantially "U"-shaped tube having a sample input port at a first end of the "U"-shaped tube, a sample output port at a second end of the "U"-shaped tube, and a light source configured to provide electromagnetic radiation through a bottom portion of the "U"-shaped tube to a detector cell.

Furthermore, although FIG. 2 illustrates operation of the cannabinoid analyzer 100 in a normal operating mode according to a first embodiment, it is to be understood that alternate implementations are within the scope of the present disclosure. For example, in alternate embodiments the analysis process may be fully automated. Responsive to receiving a sample, an alternate cannabinoid analyzer could be configured to automatically weigh the sample, combine an appropriate amount of a solvent with the sample, prepare one or more internal components for sample analysis, analyze the sample and interpret resulting data. Subsequent to the automatic analysis, results (e.g., including chemical concentration information) can be displayed on a display screen coupled to the alternate cannabinoid analyzer for review by a user.

What is claimed is:

1. A cannabinoid analysis system comprising:
   a solvent input port configured to receive a flow of a solvent;
   a sample input port configured to receive a chemical mixture including a sample;
   a pump configured to move the solvent and chemical mixture;
   an extraction cartridge coupled to the pump and configured to separate a combination of the chemical mixture and the flow of the solvent into two or more partially-separated chemical components;
   a spectroscopy cell configured to generate a chromatogram including two or more overlapping absorption peaks corresponding to the two or more partially-separated chemical components; and
   a controller configured to determine a chemical concentration of each partially-separated chemical component of the two or more partially-separated chemical components by (a) for each absorption peak overlapping with another absorption peak, quantifying an interference factor corresponding to a degree of overlap between the absorption peaks, (b) computing an area of each absorption peak, (c) correcting the computed area of an absorption peak by any interference factor associated therewith, and (d) computing the chemical concentration of each of the partially-separated chemical components based on the corresponding corrected absorption peaks, wherein the controller is further configured 1 to represent the interference factors in a square matrix and to compute the chemical concentration of each of the partially-separated chemical components based on the corresponding corrected absorption peaks by (a) inverting the matrix, (b) producing a corrected matrix from the inverted matrix, and (c) transforming the corrected matrix into relative concentration data.

2. The system of claim 1, wherein the spectroscopy cell further comprises one or both of a UV light source and an IR light source, the UV light source and the IR light source being configured to provide electromagnetic radiation to the two or more partially-separated chemical components.

3. The system of claim 2, wherein the UV light source is configured to emit electromagnetic radiation having a wavelength of 230 nm.

4. The system of claim 2, wherein
   the UV light source is configured to emit electromagnetic radiation having a wavelength of 230 nm, and
   the IR light source is configured to emit electromagnetic radiation having a wavelength of 3000 nm.

5. The system of claim 2, wherein
   the UV light source is configured to emit electromagnetic radiation having a wavelength of 230 nm, and
   the IR light source is configured to emit electromagnetic radiation having a wavelength of 3000 nm, electromagnetic radiation having a wavelength of 5000 nm, electromagnetic radiation having a wavelength of 5700 nm, electromagnetic radiation having a wavelength of 6250 nm, electromagnetic radiation having a wavelength of 6900 nm, and electromagnetic radiation having a wavelength of 8000 nm.

6. The system of claim 2, wherein the spectroscopy cell includes a silicon carbide detector configured to receive the electromagnetic radiation.

7. The system of claim 1, wherein the sample input port is configured to receive a calibration sample having a volume greater than a volume of the sample.

8. The system of claim 1, wherein the two or more chemical components include two or more of cannabidiol, cannabidiolic acid, Δ9-tetrahydrocannabinol, tetrahydrocannabolic acid, cannabinol, cannabigerolic acid and cannabichromene.

9. The system of claim 1, wherein the extraction cartridge is configured to execute a column chromatography procedure.

10. The system of claim 9, wherein the extraction cartridge is a solid phase extraction cartridge.

11. A cannabinoid analysis system comprising:
    a solvent input port configured to receive a flow of a solvent;
    a sample input port configured to receive a chemical mixture including a sample;
    a pump configured to move the solvent and chemical mixture;
    an extraction cartridge coupled to the pump and configured to separate a combination of the chemical mixture and the flow of the solvent into two or more partially-separated chemical components;
    a spectroscopy cell configured to generate a chromatogram including two or more overlapping absorption peaks corresponding to the two or more partially-separated chemical components; and
    a controller configured to determine a chemical concentration of each partially-separated chemical component of the two or more partially-separated chemical components by (a) for each absorption peak overlapping with another absorption peak, quantifying an interference factor corresponding to a degree of overlap between the absorption peaks, (b) computing an area of each absorption peak, (c) correcting the computed area of an absorption peak by each interference factor associated therewith, and (d) computing the chemical concentration of each of the partially-separated chemical components based on the corresponding corrected absorption peaks,
    wherein the controller is further configured to operate the pump in an abnormal operating mode upon detection of an obstruction in the moving solvent and chemical mixture, whereby in the abnormal operating mode a mixture of the solvent and sample particulates is driven to exit the system via the sample input port.

* * * * *